United States Patent [19]
Prass et al.

[11] Patent Number: 5,161,533
[45] Date of Patent: Nov. 10, 1992

[54] BREAK-APART NEEDLE ELECTRODE SYSTEM FOR MONITORING FACIAL EMG

[75] Inventors: Richard L. Prass, Virginia Beach, Va.; George C. Robertson, Ponte Vedra Beach, Fla.

[73] Assignee: Xomed-Treace Inc., Jacksonville, Fla.

[21] Appl. No.: 762,182

[22] Filed: Sep. 19, 1991

[51] Int. Cl.$^5$ ............................................. A61B 5/04
[52] U.S. Cl. .................................. 128/639; 128/733
[58] Field of Search ............... 128/733, 734, 731, 639, 128/640, 642, 643, 644, 783, 784, 804, 419 R, 420.5, 421, 741; 606/32, 41, 48, 49, 50, 129

[56] References Cited

U.S. PATENT DOCUMENTS

| | | | |
|---|---|---|---|
| 3,057,356 | 10/1962 | Greatbatch | 128/419 PG |
| 3,212,496 | 10/1965 | Preston | 128/725 |
| 3,313,293 | 4/1967 | Chesebrough et al. | 128/733 |
| 3,682,162 | 8/1972 | Colyer | 128/741 |
| 4,155,353 | 5/1979 | Rea et al. | 128/642 |
| 4,233,987 | 11/1980 | Feingold | 128/639 |
| 4,510,939 | 4/1985 | Brenman et al. | 128/639 |
| 4,517,983 | 5/1985 | Toyosu et al. | 128/639 |
| 4,537,198 | 8/1985 | Corbett | 128/639 |
| 4,920,968 | 5/1990 | Takase | 128/639 |
| 5,024,228 | 6/1991 | Goldstone et al. | 128/642 |

Primary Examiner—Max Hindenburg
Assistant Examiner—Guy V. Tucker
Attorney, Agent, or Firm—Rodman & Rodman

[57] ABSTRACT

The break-apart needle electrode system includes a pair of needle electrodes housed together in a fixed spaced-apart relationship. The needle electrodes are joined to electrical conductive wire for detachable connection to an electrical source. The needle electrodes are used in intraoperative facial nerve monitoring by facial electromyographic recording. Since the needle electrodes are furnished as a bipolar pair with twisted leads in a single break-away housing, they provide standardization, ease of placement and close bipolar recording. In instances where separate placement of needle electrodes is desired, the housing can be broken apart at a break-away joint. The needle electrodes are easily manipulated at the housing section as a tandem unit or as separate entities after the housing is broken apart.

18 Claims, 1 Drawing Sheet

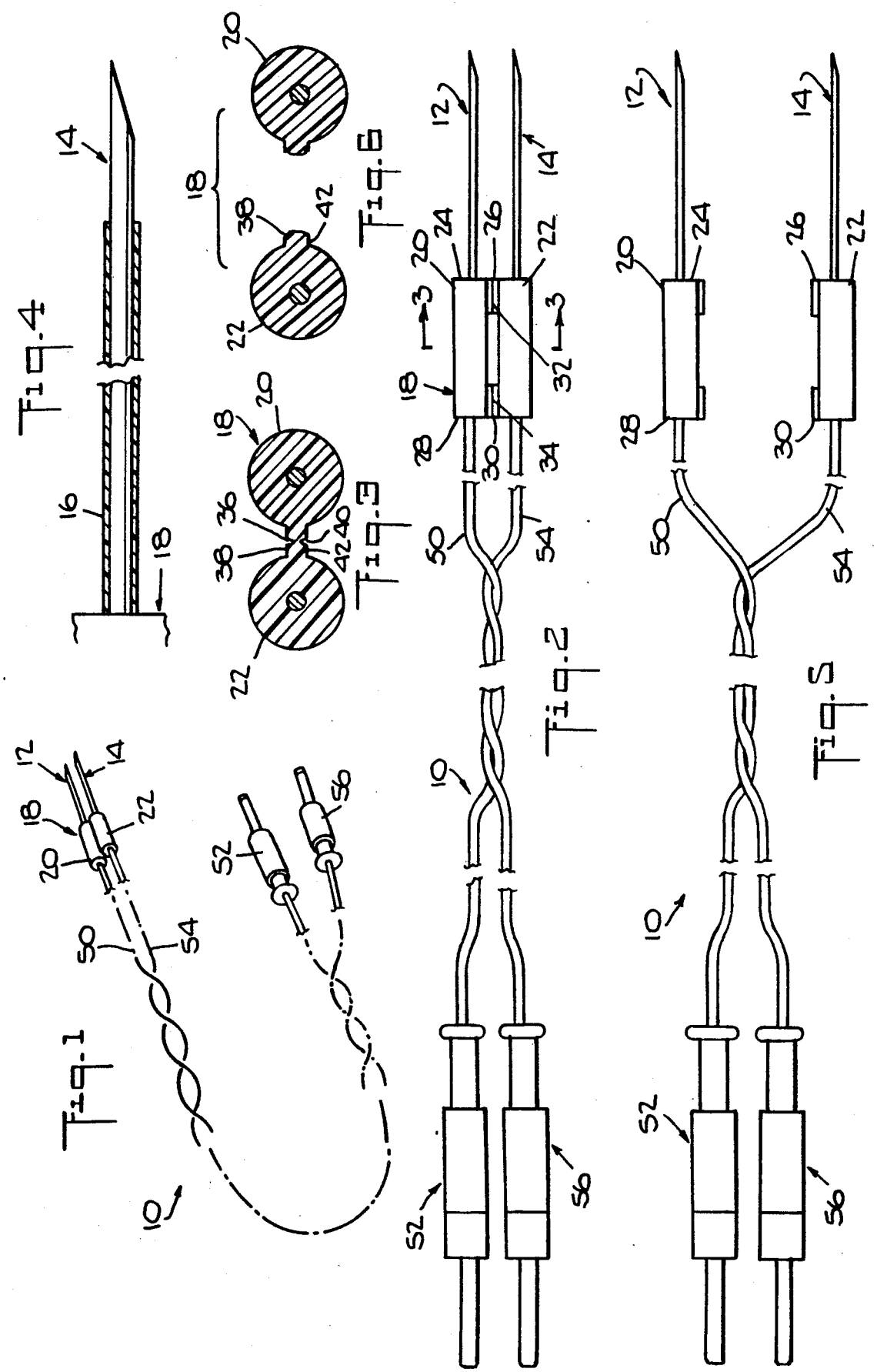

BREAK-APART NEEDLE ELECTRODE SYSTEM FOR MONITORING FACIAL EMG

BACKGROUND OF THE INVENTION

This invention relates to needle electrodes for recording electromyographic activity and more particularly to a set of paired needle electrodes, having a fixed spaced relationship from each other, which can be separated or broken apart when desired.

Needle electrodes which can be used for recording facial electromyographic activity for the purpose of intraoperative facial nerve monitoring include surface electrodes, monopolar and concentric electromyographic needle electrodes and electroencephalographic needle electrodes as well as wire.

Recording needle electrodes may be placed in a close relationship or a relatively distant arrangement. Proponents of distantly spaced recording needle electrodes believe that such arrangement is more sensitive in representing a relatively greater amount of facial musculature. However, the relatively distant arrangement of needle electrodes is also sensitive in detecting electrical artifacts and false positive responses. Proponents of recording needle electrodes having relatively close proximity to each other such as 0.5 cm. apart, generally do not report a lack of recording sensitivity.

Standard bipolar or concentric needle electrodes and monopolar electromyographic needle electrodes are generally not as favored as electroencephalographic needle electrodes in recording facial electromyographic activity, presumably because electroencephalographic needle electrodes usually have a broader area of contact of facial musculature and generally indicate a greater overall sensitivity. However, electroencephalographic needle electrodes provide variations in signal quality, especially in cases of excessively thick skin and subcutaneous tissue over the facial muscles. This variation in signal quality may be due to significant parallel contact of the needle electrodes to inactive tissue with relatively less area of the needle electrode actually inside the facial muscle tissue.

Wire electrodes provided with needles of 1 inch to 1.5 inch length can circumvent this problem by placement o the entire contact area of the wire electrode inside the facial muscles. The length of the wire electrode used for insertion allows the wire electrode to be placed parallel to the plane of the facial muscles. Thus the chance of broad contact of the wire electrode to facial muscle is maximized. However, wire electrodes of adequate quality are not commercially available and are usually fabricated by individual practitioners. Furthermore, the delicate nature of wire electrodes is such that they are difficult to use and are often used only once.

At present there is no standard method of arranging wire leads from the needle electrode back to the patient connector box. Some practitioners use long leads while others employ short leads with harnesses that have a twisted pair arrangement of the wires in a given bipolar pair.

It is known that inadequate care in the arrangement of the low signal high impedance needle electrode leads may lead to enhanced "antenna-like" qualities of the input and result in excessive sensitivity to electrical artifacts. Thus the lack of standard methodology for facial electromyographic recording in intraoperative facial nerve monitoring can lead to disparate results and adversely affect the apparent reliability of the technique and/or equipment associated with such recording.

It is thus desirable to provide an intramuscular facial nerve recording needle electrode which is simple to use and permits reliable placement yet provides high quality and sensitive recording of facial electromyographic activity. It is also desirable that the needle electrode permit ease of insertion, have the requisite sensitivity, be reusable and provide high quality recorded signals that are available with wire electrodes.

OBJECTS AND SUMMARY OF THE INVENTION

Among the several objects of the invention may be noted the provision of a novel arrangement of intramuscular facial nerve recording needle electrodes, a novel arrangement of intramuscular facial nerve recording needle electrodes that provides high quality and sensitive recording of facial electromyographic activity, a novel arrangement of intramuscular facial nerve recording needle electrodes that can be easily inserted in body tissue, have high sensitivity and are reusable, a novel tandem arrangement of intramuscular facial nerve recording needle electrodes that can be used for simultaneous insertion in body tissue, a novel tandem arrangement of intramuscular facial nerve recording needle electrodes that can be broken apart when desired for individual placement in body tissue and a novel method of recording facial electromyographic activity.

Other objects and features of the invention will be in part apparent and in part pointed out hereinafter.

. In accordance with the invention, the needle electrode system includes a pair of needle electrodes joined together in a break-away housing formed of insulating material. An electrically conductive wire is connected to each needle electrode and extends from the housing to connection means for connection to an electrical source. The housing for the needle electrodes includes a break-away link or joint of reduced thickness relative to the housing section that surrounds each needle electrode.

The needle electrodes are sufficiently integral with each other to permit simultaneous use, as for example in the recording of facial electromyographic activity.

When it is desired to use the needle electrodes separately from each other, the housing can be broken apart at the break-away joint. Once the needle electrodes are separated, each needle electrode can be individually manipulated via the housing.

The invention accordingly comprises the constructions and method hereinafter described, the scope of the invention being indicated in the claims.

DESCRIPTION OF THE DRAWING

In the accompanying drawing,

FIG. 1 is a simplified schematic perspective view of a break-apart needle electrode system incorporating one embodiment of the invention;

FIG. 2 is an enlarged plan view thereof;

FIG. 3 is a sectional view taken on the line 3—3 of FIG. 2;

FIG. 4 is an enlarged fragmentary detail of a needle electrode thereof;

FIG. 5 is a view similar to FIG. 2 with the needle electrodes broken away from each other; and, FIG. 6 is a view similar to FIG. 3 showing the needle electrodes in broken apart condition.

DETAILED DESCRIPTION OF THE INVENTION

A needle electrode system incorporating one invention is generally indicated by the reference number 10 in FIG. 1.

The needle electrode system 10 includes a pair of elongated needle electrodes 12 and 14 which can be formed for example, of 400 series stainless steel. The needle electrodes are approximately 2.5 cm. in length and are spaced apart approximately 5 mm. A Teflon® coating 16 can be provided on the needle electrode surface for an approximate extent of 2 cm., the remaining extent to the free end of the needle electrode being preferably uncoated.

The needle electrodes 12 and 14 are supported in a housing 18 that includes two generally cylindrical sections 20 and 22. The cylindrical sections 20 and 22 are joined together at an end 24 by a break-away link or joint 26 and at an end 28 by a break-away link or joint 30. The joints 26 and 30 are spaced from each other a predetermined amount. The thickness of the joints 26 and 30 is of substantially lesser magnitude than the diameter of the cylindrical sections 20 and 22.

A break-away line 32 is formed in the break-away link 26 and a break-away line 34 is formed in the break-away link 30. As most clearly shown in FIG. 3, the break-away line can be in the form of a stress concentration groove 36 formed in an upper surface 38 of the break-away link and a stress concentration groove 40 formed in a lower surface 42 of the break-away link. The break-away line can also be in the form of perforations or any other suitable built-in weakness.

The housing 18 is formed of a suitable insulating material and extends for approximately 15 mm. to facilitate manipulation of the needle electrodes 12 and 14.

A wire lead 50 extends from the needle electrode 12 to a standard pin connector 52 and a wire lead 54 extends from the needle electrode 14 to a standard pin connector 56. The wire leads 50 and 54 are encased in a suitable flexible insulating material such as a polyvinylchloride jacket. Preferably the wire leads 50 and 54 are detachably twisted together in a known manner.

The needle electrodes 12 and 14 are thus furnished as a bipolar pair in a single break-away housing. The twisted leads 50 and 54 help preserve common mode rejection properties of a differential amplifier (not shown) that is used in recording facial electromyographic activity.

In using the break-away needle electrode system 10, the needle electrodes 12 and 14 in the unified housing 18 permit simultaneous insertion in the facial musculature (not shown) at a fixed spatial relationship to provide a standardized placement and close bipolar recording for optimal signal to noise ratio. In instances where separate placements of needle electrodes may be preferred, the housing 18 can be broken apart at the break-away lines 32 an 34 to permit separate placement of the needle electrodes 12 and 14. The Teflon® coating 16 provided on the needle electrodes 12 and 14 facilitates insertion thereof in the facial musculature. In addition, the Teflon® coated needle electrode provides an insulation that improves signal quality by eliminating parallel contact with inactive tissue such as skin and subcutaneous tissue. The length of the uninsulated tip of the needle electrodes 12 and 14 provides a broad area of contact to facial musculature for increased sensitivity.

If desired, the needle electrodes 12 and 14 can be used for other applications such as masseter, sternocleidomastoid and anterior trapezius muscle recording.

The break-away lines 32 and 34 in the break-away links 26 and 30 facilitate the separation or breaking apart of the cylindrical sections 20 and 22 when it is desired to separate the needle electrodes 12 and 14. The break-away links 26 and 30 are also sized to provide sufficient integrity between the cylindrical sections 20 and 22 to permit use of the needle electrodes 12 and 14 as a tandem pair.

Some advantages of the invention evident from the foregoing description include a fixed paired electromyographic needle electrode system that can be used in tandem as a single unit or the tandem needle electrodes can be broken away from each other for separate placement of the needle electrodes. The break-away housing permits easy manipulation of the needle electrodes as a pair or as individual needle electrodes and the relatively long length of the needle electrode permits use of a relatively long length of uninsulated tip to provide a broad area of contact to facial musculature for increased sensitivity. The Teflon® coating on the needle electrode also provides insulation which improves signal quality by elimination of parallel contact with inactive tissue. The break-away housing provides for standardized spacing, ease of placement and close bipolar recording for optimal signal to noise ratio.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A needle electrode system comprising,
   a) a pair of needle electrodes,
   b) an electrically conductive wire joined to each needle electrode to permit electrical conduction through said needle electrodes from said electrically conductive wires, each said electrically conductive wire including connection means for connection to an electrical source to permit electrical conduction through respective said needle electrodes from respective said wires,
   c) means for joining said needle electrodes together in a predetermined spaced relationship for simultaneous insertion of said needle electrodes into a body tissue,
   d) said joining means including a break-apart joint for permitting said needle electrodes to be separated from each other to allow separate insertion of said needle electrodes into a body tissue at a selected spacing from each other.

2. The needle electrode system as claimed in claim 1 wherein said break-apart joint includes a preformed breakable section of predetermined thickness.

3. The needle electrode system as claimed in claim 1 wherein said means for joining said needle electrodes together include a housing which receives said needle electrodes and holds said needle electrodes in said predetermined spaced relationship, said break-apart joint constituted by a perforate section in said housing.

4. The needle electrode system as claimed in claim 3 wherein said housing is formed of an insulating material and extends longitudinally of said needle electrodes to permit manipulation of said needle electrodes.

5. The needle electrode system as claimed in claim 4 wherein said break-apart joint is formed to divide said housing into two subhousings, each said subhousing receiving a respective said needle electrode and each said subhousing being independently movable when said break-apart joint is broken apart.

6. The needle electrode system as claimed in claim 1 wherein a predetermined portion of said needle electrode is coated with a friction reducing material.

7. The needle electrode system as claimed in claim 6 wherein said coating is formed of a material selected from the group consisting of tetrafluoroethylene fluorocarbon resins and fluorinated ethylene-propylene resins.

8. The needle electrode system as claimed in claim 1 wherein said wires are insulated and detachably joined together to permit separation of said wires and separation of said needle electrodes when said break-apart joint is broken apart.

9. The needle electrode system as claimed in claim 1 including connection means arranged to permit bipolar connection of said needle electrodes.

10. A needle electrode system comprising,
  a) a pair of needle electrodes,
  b) a housing for joining said needle electrodes together in a fixed predetermined spaced and parallel relationship,
  c) an electrically conductive wire corresponding to each said needle electrode, each said wire having one end extending from a respective said needle electrode such that said needle electrodes, when joined together, are independently conductive,
  d) said housing including a break-apart joint to permit separation of said needle electrodes whereby said needle electrodes are separate and independently conductive.

11. The needle electrode system as claimed in claim 10 wherein said housing is structurally weakened at said break-apart joint to facilitate breakage of said housing at said break-apart joint.

12. The needle electrode system as claimed in claim 10 wherein said break-apart joint includes perforations in said housing to facilitate breakage of said housing at said break-apart joint.

13. The needle electrode system as claimed in claim 10 wherein said housing includes two subhousings joined together at said break-apart joint, said break-apart joint having a predetermined stress tolerance below that of any other part of the housing to ensure that said subhousings break apart at said break-apart joint.

14. The needle electrode system as claimed in claim 13 wherein said break-apart joint is constituted by spaced connection members joining said subhousings together, said spaced connection members being breakable at said break-apart joint.

15. The needle electrode system as claimed in claim 10 wherein said break-apart joint is provided with a stress concentration formation to facilitate breakage of said housing at said break-apart joint.

16. A method of recording facial electromyographic activity comprising,
  a) joining a pair of needle electrodes together in a fixed predetermined spacial relationship,
  b) extending electrical wires separately from each of the needle electrodes to permit independent conductive activity to each of said needle electrodes,
  c) forming a weakness in the joint that connects the needle electrodes together such that the needle electrodes can be broken apart at will while maintaining their independent electrical conductivity,
  d) inserting the needle electrodes into a body tissue and,
  e) recording facial electromyographic activity from the insertion location of the needle electrodes.

17. The method of claim 16 including maintaining the needle electrodes integrally joined to permit simultaneous insertion thereof into a body tissue.

18. The method of claim 16 including breaking apart the needle electrodes before insertion into a body tissue to permit separate insertion thereof into a body tissue.

* * * * *